(12) United States Patent
Logier et al.

(10) Patent No.: US 11,020,056 B2
(45) Date of Patent: *Jun. 1, 2021

(54) METHOD AND DEVICE FOR AUTOMATIC QUALITY CONTROL OF AN RR SERIES OBTAINED FROM A CARDIAC SIGNAL

(71) Applicant: CENTRE HOSPITALIER REGIONAL UNIVERSITAIRE DE LILLE, Lille (FR)

(72) Inventors: Régis Logier, Marquette lez Lille (FR); Julien De Jonckheere, Lomme (FR); Mathieu Jeanne, Lille (FR)

(73) Assignee: CENTRE HOSPITALIER REGIONAL UNIVERSITAIRE DE LILLE, Lille (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/378,917

(22) Filed: Apr. 9, 2019

(65) Prior Publication Data
US 2019/0231275 A1     Aug. 1, 2019

Related U.S. Application Data

(63) Continuation of application No. 15/118,417, filed as application No. PCT/FR2015/050418 on Feb. 20, 2015, now Pat. No. 10,292,660.

(30) Foreign Application Priority Data

Feb. 25, 2014 (FR) .................................... 1451488

(51) Int. Cl.
*A61B 5/02* (2006.01)
*A61B 5/00* (2006.01)
(Continued)

(52) U.S. Cl.
CPC ........ *A61B 5/7221* (2013.01); *A61B 5/02405* (2013.01); *A61B 5/02455* (2013.01);
(Continued)

(58) Field of Classification Search
CPC ... A61B 5/7221; A61B 5/746; A61B 5/02405; A61B 5/04012; A61B 5/044;
(Continued)

(56) References Cited

U.S. PATENT DOCUMENTS

2011/0270346 A1* 11/2011 Frei ..................... A61B 5/4094
607/45

OTHER PUBLICATIONS

De Jonckeere J. et al. "From Pain to Stress Evaluation using Heart Rate Variability Analysi: Development of and Evaluation Platform", 2010 Annual International Conference of the IEEE Engineering in Medicine and Biology Society: EMBC 2010); Piscataway, NJ, USA Aug. 31, 2010, pp. 5852-5855 (Year: 2010).*

* cited by examiner

*Primary Examiner* — Rex R Holmes
(74) *Attorney, Agent, or Firm* — Blue Filament Law PLLC (57) ABSTRACT

The method allows controlling the quality of an initial RR series made up of a plurality of (RRi) samples which are respectively a function of time intervals (δti) which separate two successive heartbeats. During this method, one resamples the RR series so as to obtain a resampled RR series, and one automatically controls the quality of the RR series by automatically calculating at least the mathematical norm value (NORME), in a sliding window, of the resampled RR series, said mathematical norm value being given by the following formula:

(Continued)

$$NORME = \sqrt{\sum_{i=1}^{N}\left(RR_i - \frac{1}{N}\sum_{i=1}^{N}(RR_i)\right)^2}$$

where N is the number of RRi samples in said window.

30 Claims, 2 Drawing Sheets

(51) Int. Cl.
*A61B 5/0245* (2006.01)
*A61B 5/316* (2021.01)
*A61B 5/327* (2021.01)
*A61B 5/339* (2021.01)
*A61B 5/352* (2021.01)
*A61B 5/364* (2021.01)
*A61B 5/024* (2006.01)

(52) U.S. Cl.
CPC .............. *A61B 5/316* (2021.01); *A61B 5/327* (2021.01); *A61B 5/339* (2021.01); *A61B 5/352* (2021.01); *A61B 5/364* (2021.01); *A61B 5/7405* (2013.01); *A61B 5/746* (2013.01)

(58) Field of Classification Search
CPC ... A61B 5/7405; A61B 5/0468; A61B 5/0456; A61B 5/04028; A61B 5/02455
See application file for complete search history.

METHOD AND DEVICE FOR AUTOMATIC QUALITY CONTROL OF AN RR SERIES OBTAINED FROM A CARDIAC SIGNAL

RELATED APPLICATIONS

This application is a continuation of U.S. Utility Pat. No. 10,292,660 filed Aug. 11, 2016; that in turn is a US national phase application of PCT/FR2015/050418 filed Feb. 20, 2015 that in turn claims priority benefit of French application Serial Number 1451488 filed on Feb. 25, 2014; the contents of which are hereby incorporated by reference.

FIELD OF THE INVENTION

The present invention relates to the field of digital processing of a bioelectrical signal, which is characteristic of the cardiac rhythm of a living being, and which is designated in the present text by the term cardiac signal. This is for example, but not exclusively, an electrocardiographic (ECG) signal. In this technical field, the invention relates to automatic quality control of an RR series obtained by sampling a cardiac signal.

BACKGROUND

From a physiological point of view, the heart of a living being, isolated from outside influence, contracts automatically and very regularly as does a metronome, under the action of the sinus node which generates an independent nerve impulse and, thereby, causes a spontaneous cardiac muscle contraction. The heart is not however isolated but is connected to the autonomic nervous system (ANS) via parasympathetic and sympathetic systems. The autonomic nervous system influences the activity of the heart: the sympathetic system accelerates the heart rate, while the parasympathetic system slows it down. Thus, despite a certain degree of autonomy, the heart undergoes influences from the autonomic nervous system, which allows, in particular, the body of a living being to adapt the heart rate depending on its needs, however within reasonable limits. It is understood, therefore, that the analysis of the evolution of the heart rate over time, and in particular changes in the heart rate (changes in the heart beat), provides important information on the activity of the cardiac system, particularly on the activity of the autonomic nervous system. Now, knowledge of ANS activity can be of great help in the development of a diagnosis of many clinical situations. On this subject, reference may be made, for example, to the following publication: Lacroix D, Logier R., Kacet S., Hazard J-R, Dagano J. (1992): "Effects of consecutive administration of central and peripheral anticholinergic agents on respiratory sinus arrhythmia in normal subjects, J. of the Autonomic Nervous System", Vol 39, pages 211-218.

To study these fluctuations in heart rate, various filtering techniques and spectral analysis of a signal representing the evolution over time of the instant heart rate (or frequency) have already been developed since 1970, such signal which is obtained after sampling an analog bioelectrical signal characteristic of the heartbeat of a living being, and termed afterwards "analog cardiac signal."

To acquire this cardiac signal, different techniques of invasive or non-invasive acquisition are known. One known invasive technique is, for example, to use a blood pressure sensor connected to a catheter inserted into an artery. Among the known non-invasive methods are included, for example, the use of an infrared pulse sensor, or the acquisition of an electrocardiographic (ECG) signal using an electrocardiograph. This latter method of acquiring an ECG signal is in practice the most commonly used to date, because, in addition to its noninvasive nature, it advantageously provides a more accurate signal than that which is obtained, for example, by means of an infrared pulse sensor.

Figure 3:
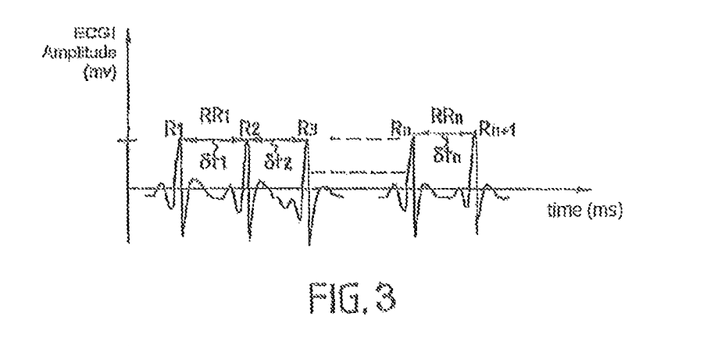
FIG. 3 shows an example of digital ECG signal obtained after sampling an analog ECG signal.

The ECG signal is known as consisting of a succession of electrical depolarizations whose appearance is shown in FIG. 3 attached. The P wave, which corresponds to the depolarization of the atria, has a low amplitude and a dome shape. The PQ space reflects the time of atrioventricular conduction. The QRS complex reflects the ventricular contraction, and the T wave the ventricular repolarization. In practice, the peak R is considered as a marker of the ventricular systole, that is to say, of the heartbeat.

In practice, the R wave usually being the finest and most extensive part of the QRS, it is generally used to locate the heart beat with very good accuracy, in practice of the order of one thousandth of a second. Thus, the time interval between two successive R waves accurately characterizes the time separating two successive heartbeats; this is the period of the ECG signal, and the inverse of this period gives the instantaneous heart rate.

To automatically construct the signal, called afterwards the RR series, representing the evolution in time of the instantaneous heart rate, the ECG signal, which is an analog signal (analog/digital conversion of the ECG signal), is sampled, and the sampled digital ECG signal is processed by automatically detecting R waves in this digital signal. An RR series is thus, in a conventional manner, comprised of a plurality of successive RRi samples (or points), each RRi sample being a function of the time interval between two successive R waves of the ECG signal.

However, it should be noted, on the one hand, that the other waves of depolarization (P, Q, S or T) of the ECG signal can also be used for characterizing the heart rate, even if the measurement accuracy is not as good as when using the R waves. On the other hand, depending on the acquisition technique chosen, the cardiac signal may have a different shape from that of the abovementioned ECG signal. The cardiac signal is not necessarily analog but may be a digital signal. Accordingly, in the present text, the term RR series is not limited to the aforementioned specific definition based on the R waves of an ECG signal, but is defined in a more general way in the context of the present invention as a series of several digital samples called $RR_i$, obtained from a cardiac signal that is characteristic of the heart rate, each RRi sample being a function of the time interval between two successive heartbeats. Each $RR_i$ sample may be proportional, and in particular equal, to the time interval between two successive heartbeats, or inversely proportional to the time interval between two successive heartbeats.

In practice, disturbances in the cardiac signal, especially in an ECG signal, induce, in the RR series issued from this cardiac signal, abrupt changes of short duration, commonly called artifacts.

Disturbances, causing artifacts in the RR series, may be physiological and intrinsically linked to a temporary malfunction of the cardiac system; it may be, for example, an extrasystole. These disturbances may also be external and not related to the functioning of the cardiac system; it may be, for example, due to a patient's movement, briefly altering the measurement signal.

Artifacts in an RR series may result in a single incorrect sample or in a plurality of successive incorrect samples. In practice, an artifact in the RR series can be likened to a Dirac pulse, and is reflected, in the frequency domain, by a rectangular continuous broadband spectrum. Therefore, assuming that a series RR could be transposed in the frequency domain (by Fourier transform or other), without first taking special precautions, the presence of artifacts in the RR series would result in the frequency domain by obtaining a very disturbed frequency spectrum of the RR series, of rectangular broadband shape, masking the spectrum of the real signal.

For this reason, to get correct frequency information, it is essential to eliminate the artifacts before performing the frequency transposition.

It was thus proposed, in international patent application WO 02/069178, as well as in the article from Logier R, De Jonckheere J, Dassonneville A., "An efficient algorithm for R-R intervals series filtering". Conf Proc IEEE Eng Med Biol Soc. 2004; 6:3937-40, digital filtering algorithms, which generally allow filtering in real time a series RR obtained from a cardiac signal, by automatically detecting in the RR series the presence of one or more successive incorrect $RR_i$ samples, and by automatically replacing in the RR series the incorrect RRi samples that were detected by corrected $RR_c$ samples. Detecting incorrect $RR_i$ samples may be performed in various ways and the corrected ($RR_e$) samples may also be calculated in various ways, and for example, and for example, but not exclusively, by linear interpolation.

A problem of these filtering algorithms, designated subsequently algorithms or filtering method "with reconstruction of incorrect samples of an RR series", lies in the fact that the reconstruction of the RR series by replacing incorrect $RR_i$ samples which were detected by corrected $RR_c$ samples, can result in a final RR series partly rebuilt which is itself partially or completely distorted, especially when the cardiac signal that was taken is of poor quality. The lack of quality of this cardiac signal may be the result of many factors, such as, for example, and in a non-limiting, non-exhaustive manner, poor positioning of the electrodes or sensors of the heart signal, insufficient signal amplification in the signal processing chain, etc . . . .

But the reconstruction of a distorted RR series has not so far been detected by the filtering algorithms in a series RR. It follows that the information provided by these filtering algorithms can be completely wrong or insignificant without anyone noticing.

PURPOSE OF THE INVENTION

The present invention aims at providing a solution for an automatic quality control of an RR series obtained from a cardiac signal.

SUMMARY OF THE INVENTION

The first purpose of the invention is thus a quality control method of an initial RR series consisting of a plurality of samples ($RR_i$) which are respectively a function of time intervals ($\delta ti$) which separate two successive heartbeats, method during which one resamples the RR series so as to obtain a resampled RR series. Characteristically, according to the invention, one automatically controls the quality of the RR series by automatically calculating, in a sliding window, of the resampled RR series, said mathematical norm value being given by the following formula:

$$NORME = \sqrt{\sum_{i=1}^{N}\left(RR_i - \frac{1}{N}\sum_{i=1}^{N}(RR_i)\right)^2}$$

where N is the number of $RR_i$ samples in said window.

In this text, and particularly in the claims, the term "cardiac signal" means any physical signal characteristic of the instantaneous heart rate (or frequency) of a living being. For the implementation of the invention, various invasive or non-invasive techniques can be used to acquire the cardiac signal. One known invasive technique consists, for example, in using a blood pressure sensor connected to a catheter inserted into an artery. Among the known non-invasive methods (and which is preferable) are, for example, one which consists in using an infrared pulse sensor, using an ultrasonic sensor for detection of the cardiac cycles, the type of sensor implemented in a carditocograph, or the acquisition of an electrocardiographic (ECG) signal. The acquisition of an electrocardiographic (ECG) signal is in practice the most commonly used method, because besides its non-invasive nature, it provides a more accurate cardiac signal than that obtained, for example, by means of an infrared pulse sensor.

In this text, and particularly in the claims, the term "RR series" generally means a series of various successive samples $RR_i$ obtained from a cardiac signal characteristic of the cardiac rhythm of a living being, each $RR_i$ sample being generally based on a time interval ($\delta ti$) between two successive heartbeats. Generally, each sample ($RR_i$) is proportional, in particular equal, to the time interval ($\delta ti$) between two successive heartbeats. Each ($RR_i$) sample may also be proportional, and more particularly equal to the inverse ($1/\delta ti$) of the time interval between two successive heartbeats.

In the preferred exemplary embodiment described below with reference to the accompanying figures, the RR series is more particularly constructed from the R waves of an ECG signal. This is not, however, limiting the invention. In the case of an ECG type cardiac signal, one can build the series called "RR" using the other depolarization waves (P, Q, S or T) of the ECG signal to construct the RR series, the accuracy not being however as good as when using the R waves of the ECG signal. Also, when the cardiac signal is not an ECG signal, the samples of the RR series are not calculated by determining the time interval ($\delta ti$) separating two successive R waves of the ECG signal, but are, more generally, determined by detecting in the cardiac signal the time interval between two successive heartbeats.

The invention also relates to a device for processing an RR series consisting of a plurality of (RRi) samples which are respectively a function of the time intervals ($\delta ti$) separating two successive heartbeats, said device being designed to automatically control the quality of the RR series by implementing the aforementioned method.

Another purpose of the invention is an acquisition and processing system of a cardiac signal, said system comprising electronic acquisition means of a cardiac signal, and electronic processing means designed for constructing an initial RR series from the cardiac signal acquired by the electronic acquisition means, said RR series consisting of a plurality of samples (RR) which are respectively a function of the time intervals ($\delta ti$) separating two successive heartbeats of the cardiac signal. Typically, according to the invention, said electronic processing means are designed to automatically control the quality of an RR series by implementing the aforementioned method.

The invention also provides a computer program comprising means for coding a computer program adapted to be executed by electronic processing means, and, when executed by electronic processing means, for implementing the aforementioned quality control method of an RR series.

BRIEF DESCRIPTION OF FIGURES

Other features and advantages of the invention will appear more clearly upon reading the detailed description below of a preferred embodiment of the method of the invention, said detailed description being given by way of nonlimiting and non-exhaustive example, with reference to the accompanying drawings in which.

DETAILED DESCRIPTION

System for Acquiring and Processing the Cardiac Signal

Figure 1:
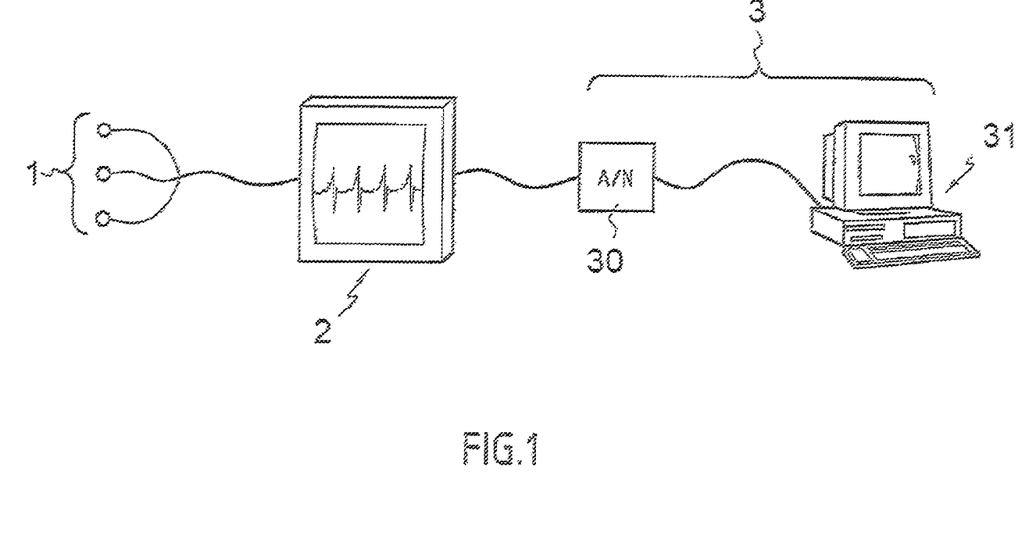
FIG. 1 schematically represents the main elements of an exemplary acquisition and processing system of an ECG signal implementing the method of the invention.

FIG. 1 shows an example of an acquisition and processing system of the cardiac signal of a living being (human or animal) that is used for the implementation of the method according to the invention.

This system comprises:
conventional electronic means for acquiring an ECG signal, comprising several measuring electrodes 1 connected at their input to an electrocardiographic (ECG) monitor 2,
electronic means 3 for processing the ECG signal outputted by the ECG monitor 2.

The processing means 3 of the ECG signal comprises an analog/digital converter 30, and an electronic processing unit 31. The input of converter 30 is connected to the output of the ECG monitor 2, and the output of the converter 30 is connected to an input port of the electronic processing unit 31. In one particular non-limiting embodiment of the invention, the processing unit 31 is constituted by a microcomputer, the converter 30 being connected to a serial port RS232 of this microcomputer. The invention is not limited to the implementation of a microcomputer as the electronic processing unit 31 can be implemented differently, for example as an FPGA type programmable electronic circuit, or as an integrated ASIC type circuit.

Figure 2:
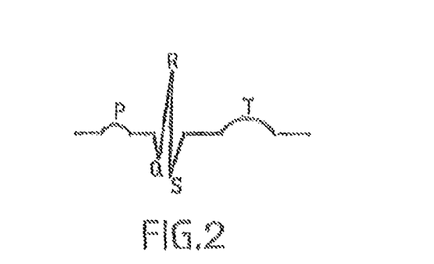
FIG. 2 represents the set of waves (PQRST) characteristic of a cardiac beat in an ECG signal.

In operation, the electrodes 1 are applied to the body of the living being, and the ECG monitor 2 outputs in the usual way an analog electrical signal, called ECG signal, that has the shape of the signal shown in FIG. 2 for each heartbeat.

Referring to FIG. 2, for each heartbeat, this electrocardiographic (ECG) signal consists of a set of electric waves:
the P wave, which corresponds to the depolarization of the atria, and which has a small amplitude and a dome shape;
the PQ space which reflects the time of atrioventricular conduction;
the R wave, regarded in practice as a marker of ventricular systole, or the heartbeat, the QRS complex reflecting ventricular contraction, and
the T wave which reflects ventricular repolarization.

This analog ECG signal is digitized by the converter 4 with a predetermined sampling frequency (fc), equal for example to 256 Hz.

The sampled signal output from the converter 30 (signal shown in FIG. 3) is processed by the processing unit 31 by means of specific processing software (filtering software) which is described in detail below. This filtering software is stored in memory of the processing unit 31 and allows, when executed, automatically constructing, from the digital signal delivered by the analog/digital converter 30, an RR series with, optionally, automatic reconstruction of incorrect samples RRi, and automatically calculating a NivQual quality index that can control the quality of the RR series, optionally partly reconstructed.

A preferred variant of this filtering software will now be detailed.

Example of Filtering Software Algorithm

In a particular variant embodiment of the invention, the main successive steps of the filtering algorithm are the following:

1. Acquisition and construction of RRi samples from the signal output from the analog/digital converter 30.
2. Filtering the RR series with optional automatic detection of incorrect samples RRi, and substituting with reconstructed samples identified in the RRc samples series.
3. Re-sampling of the RR series to a predefined frequency f to obtain resampled RRi samples.
4. Selection of RRi samples included in a time window of n seconds (n>1/f).
5. Calculating a NivQual quality index
6. Offsetting, with a time step equal to p seconds (preferably p<n), the time window of n seconds, and reiterating the calculation from step 2. This offset corresponds to the sliding of the time window for selecting the samples.

In practice, the system can be programmed to be used in real time or delayed time.

When the system is used in delayed time, step 1 is performed first in real time so as to build all RRi samples over all the period of analysis desired; all of these successive RRi samples are stored in memory, for example in a memory acquisition file of the processing unit 31. Secondly, the steps 2-6 are performed in a loop, offline, on the RRi samples stored in the acquisition file.

When the system operates in real time, step 1 of construction of the RRi samples on the one hand, and the other processing steps 2-6 on the other hand, are performed by two separate software modules operating in parallel, the first construction module (step 1) supplying the second processing and calculation module (steps 2-6) for example through a buffer file or register or equivalent.

Steps 1-5 will now be detailed.

Step 1: Acquisition and Construction of RRi Samples

The acquisition and construction of the RRi samples are performed by a first software sub-module which is input with the successive digital data constituting the digitized ECG signal (signal of FIG. 3) output by the analog digital converter 30. Each data (or point) of the ECG signal is determined by the instantaneous amplitude ECGi of the ECG signal, and by sampling time $t_i$ ($t_i=n_i/fc$, with $n_i$ being the sample number and fc representing the sampling frequency of the converter 30).

Figure 4:
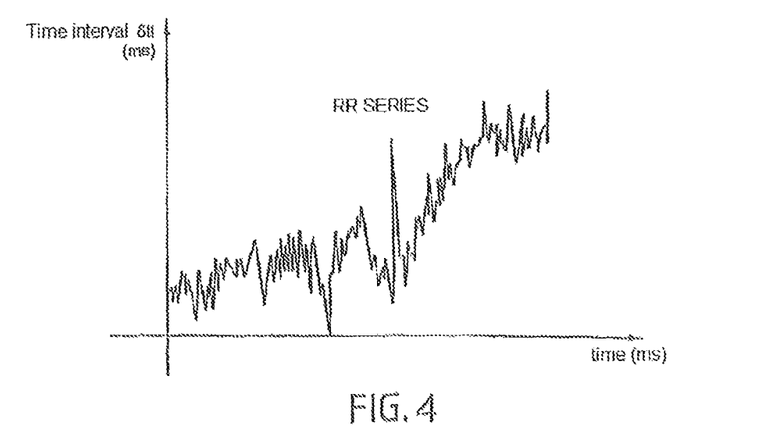
FIG. 4 shows an example of an RR series (still designated as RR signal) constructed from the signal of FIG. 3.

The first acquisition sub-module of RRi samples is designed to automatically detect each successive R, peak in the digital signal delivered by the converter 30, and to automatically construct an RR series (FIG. 4) consisting of a succession of RRi samples. Each RRi sample is defined by the pair of coordinates: $t_i$ [a sampling moment (or number)]; a time interval δti (expressed as a multiple of the sampling frequency fc) separating a peak Ri from the next peak $R_{i+1}$ (in another embodiment it could be the previous peak $R_{i-1}$).

In the usual manner, the R wave usually being the finest and most extensive part of the QRS, it is preferably used to detect heart beat with very good accuracy, the time interval δti corresponding in practice to the time between two successive heartbeats. However, in another variant, one might consider using other waves (such as Q wave or S wave) of a heartbeat of the ECG signal to detect and construct the RR series. In another variant, one could also consider using other cardiac signals such as the plethysmograph waveform or the invasive blood pressure.

Step 2: Filtering the RR Series with Optional Automatic Detection of Incorrect RRi Samples and Replacement by RRc Reconstructed Samples This filtering step consists generally in automatically detecting in the RR series the presence of one or more incorrect successive $RR_i$ samples, and automatically replacing in the RR series the incorrect $RR_i$ samples that were detected by reconstructed RRc samples. The number of reconstructed RRc samples is, most of the time, different from the number of incorrect samples that were detected.

This filtering step with automatic reconstruction of incorrect $RR_i$ samples is known per se, and examples of implementation of this filtering step are described for example in international patent application WO 02/069178, as well as in the article Logier R, De Jonckheere J, Dassonneville A., «An efficient algorithm for R-R intervals series filtering». Conf Proc IEEE Eng Med Biol Soc. 2004; 6:3937-40.

It should however be noted that in the context of the invention, the detection of incorrect RRi samples is not limited to the detection methods described in the two aforementioned publications, and reconstructed RRc samples can also be calculated in various ways, such as, for example but not exclusively, by linear interpolation, as described in the two abovementioned publications.

Each reconstructed RRc sample of the RR series is identified, for example by an associated flag type identification variable. Thus, after this step, the RR series consists of $RR_i$ samples some of which are, optionally, identified by their identification variable as reconstructed RRc samples.

Step 3: Resampling of the RR Series to a Predefined Frequency f to Obtain Resampled RRi Samples The filtered RR series (FIG. 4) supplied by the aforementioned first sub-module is automatically resampled by a second software sub-module at a predefined frequency f, which is preferably lower than the sampling frequency fc (for example, for a sampling frequency fc equal to 250 Hz, the resampling frequency f will be set to 8 hz). The purpose of this resampling is to output an RR series whose $RR_i$ samples are equidistant from a temporal point of view, that is to say, in other words an RR series in which the sampling instants are regular. This resampling is carried out in known manner by interpolation, for example by linear interpolation.

During this resampling, each reconstructed RRc sample is replaced, as appropriate, by one or more reconstructed and resampled RRrc samples.

Each reconstructed and resampled RRrc sample of the RR series is identified, for example by an associated flag type identification variable. Thus, after this step, the RR series consists of RRi samples some of which are, optionally, identified by their identification variable as reconstructed and resampled RRrc samples.

Step 4: Selection of RRi Samples (of the RR Series, Optionally Partly Reconstructed and Resampled) Included in a Main Time Window of n Seconds (n>1/f)

This step consists in isolating a number N of successive RRi samples (N=n.f.). As an indication, for example, a main window of 64 seconds (n=64) is chosen, which corresponds to 512 successive $RR_i$ samples (N=512) at a resampling frequency f of 8 hz.

The following steps are applied to the samples included in this main window.

Step 5: Calculation of a NivQual Quality Index

This step is performed using a software sub-module that automatically calculate a NivQual quality index significant of the quality of the RR series.

In the particular embodiment described in detail below, this NivQual quality index has two quality levels of 0 or 1.

More particularly, the NivQual quality index is based on two variables (FCi; NORME) which are calculated in Step 5:

1/ the value of the instantaneous heart rate ($FC_i$) calculated on each RRi sample of the RR series from Step 2, that is to say, the RR series after filtering (optionally partly reconstructed) and before resampling.

2/ the mathematical norm value (NORME) of the $RR_i$ samples of the RR series (optionally partly reconstructed and resampled) from selection Step 4 in the time window of n seconds.

The heart rate is defined by $FC_i=60000/RR_i$, where RRi is the instantaneous value of the $RR_i$ sample in millisecond.

Calculating the mathematical norm value of the RR series resampled at the frequency f n in the window of n seconds consists initially in calculating the average value M of $RR_i$ in the window.

$$M = \frac{1}{N}\sum_{i=1}^{N}(RR_i)$$

where $RR_i$ represents the value of each RR interval and N the number of samples in the window.

This average value is then subtracted at each $RR_i$ interval of the window.

$$RR_i=(RR_i-M).$$

The $RR_i$ values obtained are used for the calculation of the norm value (NORME), or:

$$NORME = \sqrt{\sum_{i=1}^{N}\left(RR_i - \frac{1}{N}\sum_{i=1}^{N}(RR_i)\right)^2}$$

An example of algorithm for calculating the NivQual quality index from the two aforementioned variables ($FC_i$; NORME) is given below:

If
    ((NORME<NormMin)
    or
    (NORME>NormMax)
    or

```
(FCi>FCMax)
    or
(FCi<FCMin)
then Nivqual = 0
IF NOT Nivqual = 1
```

The values of the FCMax, FCmin, NormMax, NormMin parameters are predefined constants, which depend, for example, on the age of the human being or depend, for example, on the animal species in the context of a veterinary application. The values of the FCMax, FCmin thresholds are those commonly used by all heart monitoring devices. The values of NormMax, NormMin thresholds of the norm value are, for example, experimentally determined on 200 individuals in each category.

By way of non-limiting example:
for a newborn: FCmax=250; FCMin=80; NormMax=3; NormMin=0
for an adult: FCMax=180; FCMin=30; NormMax=4; NormMin=0.07

The NivQual quality index calculated at each Step 5 may, for example, be displayed, especially in real time, so as to inform a practitioner of the quality level of the measured RR signal.

In the case of a NivQual quality index equal to 0, the RR series from Step 1 is considered as being of very poor quality and in fact unusable. This lack of quality of the RR series may result from many factors, such as, for example, and in a non-limiting and non-exhaustive manner, improper positioning of the electrodes 1 or the sensors for measuring the heart signal, insufficient signal amplification in the signal processing chain, etc.

When calculating a NivQual quality index equal to 0, processing unit 31 can be programmed to automatically trigger several actions, including and not limited to, triggering of a visual and/or audible alarm, and/or resetting acquisition Step 1 of $RR_i$ samples, including, in particular, a manual or automatic gain change of the source signal (ECG).

In the context of the invention, for the implementation of Step 5, this NivQual quality index calculation algorithm can be simplified by only taking into account the NORME parameter.

In another embodiment, the filtering Step 2 (detection and reconstruction of incorrect samples) may be omitted. In this case, the calculation of the norm value (NORME) and calculation of the instantaneous heart rate ($FC_i$) are performed in a sliding window directly on the samples of the initial RR series from Step 1.

The invention claimed is:

1. A method for acquiring and automatically processing a cardiac signal, said method comprising:
using an electronic acquisition device for acquiring a cardiac signal on a subject;
using a processing unit for automatically constructing a plurality of successive ($RR_i$) samples of an initial RR series from said acquired cardiac signal, where said plurality of ($RR_i$) samples being respectively a function of time intervals ($\delta t_i$) which separate two successive heartbeats in the cardiac signal, said method further comprising:
using the processing unit for automatically calculating at least a mathematical norm value (NORME), in a sliding window, of the initial RR series, said mathematical norm value being given by the following formula:

$$NORME = \sqrt{\sum_{i=1}^{N}\left(RR_i - \frac{1}{N}\sum_{i=1}^{N}(RR_i)\right)^2}$$

where N is the number of $RR_i$ samples in said window,
using the processing unit for automatically comparing the mathematical norm value with a first predefined value (NormMin) or with a second predefined value (NormMax), and for automatically triggering at least one of a visual or audible alarm when the mathematical norm value (NORME) that is calculated is smaller than said first predefined value (NormMin) or is greater than said second predefined value (NormMax), or using the processing unit for calculating a quality index (NivQual) from at least the mathematical norm value (NORME) that is calculated and for registering or displaying on a monitor said quality index (NivQual).

2. The method of claim 1, further comprising using the processing unit for automatically detecting in the initial RR series if one or more successive (RRi) samples are incorrect, and for automatically correcting, in the RR series, the one or more (RRi) samples detected as incorrect by replacing the one or more (RRi) samples detected as incorrect by one or more reconstructed (RRc) samples, so as to obtain an RR series that is partly reconstructed.

3. The method of claim 2, further comprising using the processing unit for resampling the RR series that is partly reconstructed so as to obtain a partly reconstructed and resampled RR series.

4. The method of claim 1, further comprising using the processing unit for automatically triggering at least one of a visual or audible alarm wherein when the mathematical norm value that is calculated is outside a predefined range (NormMin; NormMax).

5. The method of claim 1, further comprising using the processing unit for automatically controlling the quality of the RR series by also calculating an instantaneous heart rate FCwhere $FC_i=60000/RR_i$, $RR_i$ being the instantaneous value in millisecond of an ($RR_i$) sample of the RR series.

6. The method of claim 5, further comprising using the processing unit for automatically triggering at least one of a visual or audible alarm when the instantaneous heart rate $FC_i$ that is calculated is lower than a predefined value (FCMin).

7. The method of claim 5, further comprising using the processing unit for automatically triggering at least one of a visual or audible alarm when the instantaneous heart rate $FC_i$ that is calculated is greater than a predefined value (FCMax).

8. The method of claim 5, further comprising using the processing unit for automatically triggering at least one of a visual or audible alarm when the instantaneous heart rate $FC_i$ that is calculated is outside of a predefined range (FCMin, FCMax).

9. The method of claim 1, further comprising resetting the acquisition and construction of the ($RR_i$) samples of the initial RR series when the mathematical norm value (NORME) that is calculated is smaller than said first predefined value (NormMin).

10. The method of claim 1, further comprising resetting the acquisition and construction of the ($RR_i$) samples of the initial RR series when the mathematical norm value (NORME) that is calculated is greater than said second predefined value (NormMax).

11. The method of claim 1, further comprising resetting the acquisition and construction of the ($RR_i$) samples of the initial RR series when the mathematical norm value (NORME) that is calculated is outside a predefined range (NormMin; NormMax).

12. The method of claim 1, further comprising using the processing unit for calculating at least one (NivQual) quality index from the instantaneous heart rate $FC_i$, with $FC_i=60000/RR_i$, $RR_i$ being the instantaneous value in millisecond of a (RRi) sample of the RR series.

13. The method of claim 1, wherein the acquisition and construction of successive ($RR_i$) samples of the initial RR series from a cardiac signal is performed in real time and wherein optional resampling and automatic quality control of the RR series are performed in real time while said acquisition and construction of the successive ($RR_i$) samples of the initial RR series are taking place.

14. An acquisition and processing system for a cardiac signal, said system comprising an electronic acquisition device with a processing unit configured for acquiring a cardiac signal, and where said processing unit is configured to automatically construct an initial RR series from a cardiac signal acquired with the electronic acquisition device, said RR series comprising a plurality of (RRi) samples which are respectively a function of time intervals ($\delta ti$) which separate two successive heartbeats of the cardiac signal, wherein said processing unit is configured to implement the method of claim 1.

15. A computer program adapted to be executed by a processing unit, and allowing, when executed by said processing unit to implement the method of claim 1.

16. A method for acquiring and automatically processing a cardiac signal, said method comprising:
using an electronic acquisition device for acquiring a cardiac signal on a subject;
using a processing unit for automatically constructing a plurality of successive ($RR_i$) samples of an initial RR series from said acquired cardiac signal, said plurality of ($RR_i$) samples being respectively a function of time intervals ($\delta ti$) which separate two successive heartbeats in the cardiac signal; and
using the processing unit for resampling the RR series so as to obtain a resampled RR series, and where said method further comprises:
using the processing unit for automatically calculating at least a mathematical norm value (NORME) of the resampled RR series in a sliding window, said mathematical norm value being given by the following formula:

$$NORME = \sqrt{\sum_{i=1}^{N}\left(RR_i - \frac{1}{N}\sum_{i=1}^{N}(RR_i)\right)^2}$$

where N is the number of $RR_i$ samples in said window; and
using the processing unit for automatically comparing the mathematical norm value with a first predefined value (NormMin) or with a second predefined value (NormMax), and using the processing unit for automatically triggering at least one of a visual or audible alarm when the mathematical norm value (NORME) that is calculated is smaller than said first predefined value (NormMin) or is greater than said second predefined value (NormMax), or using a processing unit for calculating a quality index (NivQual) from at least the mathematical norm value (NORME) that is calculated and for registering or displaying on a monitor said quality index (NivQual).

17. The method of claim 16, further comprising using the processing unit for automatically detecting in the initial RR series if one or more successive (RRi) samples are incorrect, and for automatically correcting, in the RR series, the one or more (RRi) samples detected as incorrect by replacing the one or more (RRi) samples detected as incorrect by one or more reconstructed (RRc) samples, so as to obtain an RR series partly reconstructed.

18. The method of claim 17, comprising using the processing unit for resampling the RR series that is partly reconstructed so as to obtain a partly reconstructed and resampled RR series.

19. The method of claim 16, further comprising using the processing unit for automatically triggering at least one of a visual or audible alarm wherein when the mathematical norm value that is calculated is outside a predefined range (NormMin; NormMax).

20. The method of claim 16, further comprising using the processing unit for automatically controlling the quality of the RR series by also calculating an instantaneous heart rate $FC_i$, where $FC_i=60000/RR_i$, $RR_i$ being the instantaneous value in millisecond of an (RRi) sample of the RR series.

21. The method of claim 20, further comprising using the processing unit for automatically triggering at least one of a visual or audible alarm when the instantaneous heart rate $FC_i$ that is calculated is lower than a predefined value (FCMin).

22. The method of claim 20, further comprising using the processing unit for automatically triggering at least one of a visual or audible alarm when the instantaneous heart rate $FC_i$ that is calculated is greater than a predefined value (FCMax).

23. The method of claim 20, further comprising using the processing unit for automatically triggering at least one of a visual or audible alarm when the instantaneous heart rate $FC_i$ that is calculated is outside of a predefined range (FCMin, FCMax).

24. The method of claim 16, further comprising resetting the acquisition and construction of the ($RR_i$) samples of the initial RR series when the mathematical norm value (NORME) that is calculated is smaller than said first predefined value (NormMin).

25. The method of claim 16, further comprising resetting the acquisition and construction of the ($RR_i$) samples of the initial RR series when the mathematical norm value (NORME) that is calculated is greater than said second predefined value (NormMax).

26. The method of claim 16, further comprising resetting the acquisition and construction of the ($RR_i$) samples of the initial RR series when the mathematical norm value (NORME) that is calculated is outside a predefined range (NormMin; NormMax).

27. The method of claim 16, further comprising using a processing unit for calculating at least one (NivQual) quality index from the instantaneous heart rate $FC_i$, with $FC_i=60000/RR_i$, $RR_i$ being the instantaneous value in millisecond of a (RRi) sample of the RR series.

28. The method of claim 16, wherein the acquisition and construction of successive ($RR_i$) samples of the initial RR series from a cardiac signal is performed in real time and wherein optional resampling and all the other steps are performed in real time while said acquisition and construction of the successive ($RR_i$) samples of the initial RR series are taking place.

29. An acquisition and processing system for a cardiac signal, said system comprising an electronic acquisition device configured for acquiring a cardiac signal, and a processing unit configured to automatically construct an initial RR series from a cardiac signal acquired with the electronic acquisition device, said RR series comprising a plurality of (RRi) samples which are respectively a function of time intervals (δti) which separate two successive heartbeats of the cardiac signal, wherein said processing unit is configured to implement the method of claim 16.

30. A computer program adapted to be executed by a processing unit, and allowing, when executed by said processing unit to implement the method of claim 16.

* * * * *